US005700901A

United States Patent [19]

Hurst et al.

[11] Patent Number: 5,700,901
[45] Date of Patent: Dec. 23, 1997

[54] RESORBABLE MOULDINGS AND PROCESS FOR PRODUCING THEM

[75] Inventors: Achim Hurst; Wladis Winkler-Gwienek, both of Tuttlingen; Berthold Buchholz, Ingelheim am Rhein; Dieter Bendix, Ingelheim am Rhein; Gunther Entenmann, Ingelheim am Rhein, all of Germany

[73] Assignee: Boehringer Ingelheim KG, Ingelheim am Rhein, Germany

[21] Appl. No.: 371,313

[22] Filed: Jan. 11, 1995

Related U.S. Application Data

[63] Continuation of Ser. No. 237,975, May 2, 1994, abandoned, which is a continuation of Ser. No. 65,042, May 27, 1993, abandoned, which is a continuation of Ser. No. 942,534, Sep. 9, 1992, abandoned, which is a continuation of Ser. No. 824,662, Jan. 23, 1992, abandoned, which is a continuation of Ser. No. 535,813, Jun. 8, 1990, abandoned.

[30] Foreign Application Priority Data

Jun. 9, 1989 [DE] Germany .................... 39 18 861.2

[51] Int. Cl.⁶ .................... C08G 63/08; C08F 6/00
[52] U.S. Cl. .................. 528/354; 528/480; 528/481; 528/499; 528/355
[58] Field of Search ................ 528/480, 481, 528/499, 354, 355

[56] References Cited

U.S. PATENT DOCUMENTS

| | | | |
|---|---|---|---|
| 4,744,365 | 5/1988 | Kaplan | 128/335.5 |
| 4,810,775 | 3/1989 | Bendix et al. | 528/480 |
| 4,960,866 | 10/1990 | Bendix et al. | 528/499 |
| 4,983,745 | 1/1991 | Muller et al. | 528/354 |

FOREIGN PATENT DOCUMENTS

| | | |
|---|---|---|
| 0107591 | 5/1984 | European Pat. Off. . |
| 0185453 | 6/1986 | European Pat. Off. . |
| 0209371 | 1/1987 | European Pat. Off. . |
| 0349656 | 1/1990 | European Pat. Off. . |

*Primary Examiner*—Shelley A. Dodson
*Attorney, Agent, or Firm*—Robert P. Raymond; Alan R. Stempel; Mary-Ellen Devlin

[57] ABSTRACT

The invention relates to resorbable mouldings and processes for producing them.

24 Claims, No Drawings

RESORBABLE MOULDINGS AND PROCESS FOR PRODUCING THEM

This is a Continuation of application Ser. No. 237,975, filed, May 2, 1994, now abandoned which is a continuation of application Ser. No. 065,042, filed May 27, 1993, now abandoned which is a continuation of application Ser. No. 942,534, filed Sep. 9, 1992, now abandoned, which is a continuation of application Ser. No. 824,662, filed Jan. 23, 1992, now abandoned, which is a continuation of application Ser. No. 535,813, filed Jun. 8, 1990, now abandoned.

This invention relates to resorbable mouldings (implants) and the substances or mixtures of substances and methods used to produce these mouldings (implants).

Internal metallic fixation systems have become commonplace worldwide for the treatment of fractures. The bone fragments can be immobilised by plate osteosynthesis. The aim of this technique is to ensure that the fracture can heal undisturbed.

However, the use of metal implants has certain disadvantages. To prevent corrosion and foreign body reactions, the metal parts have to be removed again in a second operation after about a year. In plate osteosynthesis the rigid metal plate interferes with remodelling reconstruction processes in the region of the fracture. The consequence is atrophy of the bone caused by inactivity, which can lead to another fracture after the implant has been removed. Furthermore, metal implants make it difficult to monitor the healing of the fracture by radiology.

To overcome the disadvantages of metal implants it has frequently been proposed that the implants should be made from resorbable materials. Such materials are characterised in that they are biodegradable. In spite of their lower modulus of elasticity, compared with metals, implants of resorbable material are suitable for treatment of bone fracture.

The prerequisite is that the mechanical properties should be adapted to the particular requirements of the case. Owing to the resorbability of the material the patients are spared a second operation, the risks involved and further absence from work. The widespread introduction of resorbable implants in surgery will therefore result in a substantial reduction in costs.

The demands made of resorbable osteosynthesis implants are many. The basic prerequisites for medical use of resorbable materials are good compatibility with the tissue, toxicological safety of the polymer and their breakdown products and the sterilisability of the implants. In addition to being adequately rigid, the implants should also be plastically deformable. The elongation after fracture should be at least 2% and preferably at least 3%, so that, for example, osteosynthesis plates can be adapted to fit the individual bone shape in the operating theatre. This minimum elongation also ensures sufficient protection against brittle fracture before the yield point is reached. Elements which are particularly prone to fracture are fastening elements in which there are boreholes (e.g. osteosynthesis plates) or fairly large changes in cross-section (e.g. screws). As a result of the notch effect, stresses and stress peaks can be produced which a brittle material would be unable to withstand by deformation.

Numerous materials are known which can be degraded in the body. Of these materials, polymers and copolymers of lactic acids and glycolic acid have achieved particular significance owing to their well- known compatibility.

Thus, surgical objects, particularly osteosynthesis plates, screws and other fastening elements made of these polymers have been described in numerous published specifications. The embodiments which correspond to the prior art do, however, have numerous disadvantages:

EP 0108635, for example, shows that poly(L-lactide) with a high inherent viscosity is preferably suited to the production of surgical implants. To produce it, L-lactide is polymerised under conditions which have to be adhered to strictly, particularly with very long reaction times. The test pieces obtained from the polymers by mechanical working have a tensile strength of $58.2 N/mm^2$ with an inherent viscosity of 7.4 dl/g. With an inherent viscosity of 3.7 dl/g, the strength is only $28.8 N/mm^2$. Furthermore, the implants produced in this way have a microporous structure (cf. J. W. Leenslag, A. J. Pennings Commun. 28 92–94 (1987), Makromol. Chem. 188, 1809–1814 (1987)). This makes it easier for water to penetrate and accelerates the decomposition and loss of mechanical strength. Thus, the tensile strength of the polymers described above is only about 13 to 16% of its initial value after 12 weeks at 37° C. in buffer solution. Surgical implants are produced from polymers prepared according to EP 0108635 by machining processes. During machining, striation and other damage appears on the surface of the implants, which can lead to cracks and consequently failure of the components under static or dynamic stress and particularly under impact stress.

In the course of the hydrolytic degradation of surgical implants, the strength decreases, as is well known. In the case of microporous material, according to EP 0108635, the reduction in strength is particularly rapid (cf. for example Eitenmüller et al., Chirurg 58, 831–839 (1987)).

Various types of elongation are distinguished. A characteristic measurement of toughness and the residual deformability of a material is its percentage elongation after fracture. The elongation after fracture is the permanent change in length, compared with an initial measured length, after breakage of a sample subjected to tension.

Under stress, poly(L-lactide) exhibits brittle characteristics. The percentage elongation is only about 2% (M. Vert et al., Makromol. Chem. Suppl. 5, 30–41 (1981)). Under rapidly alternating loads there is therefore the danger of breakage of the implants. Copolymers of L-lactide have a higher elongation than poly(L-lactide) itself. In any case, the strength is known to decrease as the proportion of comonomer increases (cf. for example U.S. Pat. No. 3736646). Vert et al. (Macromol. Biomat. 1984, 119–142) give a tensile strength of $58 N/mm^2$ for an elongation of 2.1% for poly(L-lactide) and a tensile strength of $46 N/mm^2$ and an elongation at break of 3.2% for poly(L-lactide-co-D,L-lactide) 50:50; however, mouldings having this composition have the serious disadvantage that their original strength has fallen to half its original level within only two weeks.

The addition of comonomers during polymerisation therefore does increase the percentage elongation but at the same time it undesirably reduces the initial strength and the retention of strength. These disadvantages have resulted in the proposal (Vert et al., Macromolecular Biomaterials 1984), that surgical implants should be made from totally resorbable fibre-reinforced composite materials. Fibre reinforced composite materials of this kind and the production thereof are described for example in WO 88/00533, WO 87/00059 or EP 0011528. The use of non-resorbable reinforcing elements was also proposed, for example, in U.S. Pat. No. 4,329,743. However, from a technical point of view the production of fibre reinforced implants is complex. This method can be used only to produce simple mouldings, preferably pins.

The aim of the present invention is to provide a resorbable moulding (implant) which in addition to having a high initial bending strength and a high initial tensile strength also has a high strength retention and optimum percentage elongation after fracture, but is technically easier to produce than fibre-reinforced implants. Resorbable implants which satisfy these criteria should be characterised not only by a sufficient initial stability but by the retention of their strength throughout the period of healing of the fracture, i.e. a period of about 6 to 8 weeks after the operation, whilst the degree of strength should still be at least 75% of the initial level 8 weeks after the implant has been put in, with an elongation after fracture of more than 2.1%. During this stage, the implants transmit the forces which are produced and immobilise the bone fragments. After healing has taken place, the materials gradually lose their strength, as a result of biological decomposition. The increasing load results in functional structuring of the bone in the fracture line by alignment of the trabeculae, corresponding to biomechanical stress. Bone atrophy caused by a non-physiological supporting effect of the implant is thereby avoided.

The object of the invention is achieved by means of a moulding characterised by the following data:

inherent viscosity <4.5 dl/g (25° C. chloroform) but >0.8 dl/g initial bending strength >90N/mm$^2$ initial tensile strength >45N/mm$^2$ elongation after fracture >2%, preferably >3% strength >75% of the initial value after 8 weeks of implantation and can be produced from polylactide or polymers of lactide with small amounts of other comonomers, preferably by injection moulding, and optionally contains defined amounts of a monomeric or polymeric additive. Mixtures of polylactide and copolymers thereof with monomeric or polymeric additives are also referred to as polymer mixtures or polymer blends.

According to the invention, the mouldings referred to hereinbefore which contain polymer mixtures are preferred.

Also preferred are mouldings of which the inherent viscosity is less than 3.5 but greater than 1 dl/g, whilst mouldings with an inherent viscosity of between 2.5 and 1.4 dl/g are particularly preferred.

Mouldings according to this invention are implants used in all branches of surgery. In bone surgery, for example, osteosynthesis plates can be inserted together with connecting elements such as screws, expanding pins or rivets for joining and temporarily fixing bone fragments. Smooth or profiled fixation pins, fixation nails or screws are suitable for the refixing of fragments of cartilage or bone. Fractures of hollow bones can be supported in the intramedullar space using medullary cavity nails until the fracture has healed. Clips for sealing blood vessels or clamps for stitching soft tissue are examples of implants which can be made from the materials according to the invention. The advantageous percentage elongation after fracture, the favourable levels of strength and retention of strength of the implant during the healing phase guarantee success of the treatment. It goes without saying that suitable design in accordance with the properties of the plastics will result in a plurality of embodiments of such objects. This list is therefore given by way of example and is by no means restrictive.

Injection moulded mouldings according to the invention have smooth surfaces even when they are of complex structure and unlike implants obtained by the mechanical working from polymer blocks, they do not have a microporous structure. Consequently, the notch effect caused by microscopic defects can be prevented.

Furthermore, the strength retention of the injection moulded samples according to the invention is significantly better: in animal trials it was shown that the strength of implanted test pieces of poly(L-lactide) block material, not produced by injection moulding, fell to 18.5% of its initial bending strength after only 8 weeks in spite of having a high inherent viscosity (specifically 7.9 dl/g).

The success of the operation can be jeopardised by this high loss of strength of the implant material even within the bone healing phase. By contrast, the injection moulded samples of poly(L-lactide) according to the invention exhibit a retention of strength which corresponds to the requirements at 97.0% of the initial strength after 8 weeks, in spite of a comparatively low inherent viscosity (specifically 1.65 dl/g) (Example 1). The polymers used to produce the moulding according to the invention, e.g. polylactide, copolymers or the polymer mixtures according to the invention generally have an inherent viscosity of less than 4.5 dl/g, preferably less than 3.7 dl/g and, in particular, less than 3.0 dl/g, but should be not less than 1.0, preferably not less than 1.4 dl/g.

Depending on the conditions of the process, injection mouldings results in greater or lesser thermal decomposition of the polymer and consequently a reduction in its inherent viscosity. It is known that moisture and a residual content of monomer promote thermal decomposition. It will therefore readily be understood that before use the polymers should be carefully cleaned and dried using methods known per se, such as extraction or reprecipitation and/or heating in vacuo. However, it has surprisingly been found that in spite of their reduced inherent viscosity injection moulded parts have just as high an initial strength as samples from polymer blocks (Example 2). The use of implants of poly(L-lactide) with a low inherent viscosity is particularly advantageous because the resorption time is shorter compared with high molecular material: using in vitro experiments at elevated temperature in physiological solution it was possible to demonstrate that injection moulded test pieces of poly(L-lactide) (inherent viscosity 1.65 dl/g) hydrolyse more rapidly than samples of poly(L-lactide) copolymer (inherent viscosity 7.9 dl/g). In the case of implants of highly viscous poly(L-lactide) block material the resorption times of more than 3 years must be assumed. With injection moulded implants of the same size and strength, resorption periods of between 1.5 and 2.5 years can be expected. Thus, thermal degradation of polymers during injection moulding is tolerable to a certain extent, i.e. injection moulded polymers are less critical than block goods with regard to the purification process.

The invention further relates to both amorphous and crystalline injection-moulded samples. Samples of poly(L-lactide) obtained from blocks of polymer have levels of crystallinity of more than 75%, depending on the conditions of polymerisation. The crystallinity is determined in a known manner by measuring the melt enthalpy by differential scanning calorimetry (DSC) and comparing the result with the melt enthalpy of 100% crystalline polylactide, known from the literature. In the injection moulding process, amorphous or crystalline products may be obtained, depending on the retention time of the mouldings in the tool and the speed of cooling. In Examples 1 and 2, amorphous injection moulded samples were produced. The comparison with the crystalline test pieces from polymer blocks shows that the crystallinity has no effect on the initial strength. By contrast, the crystalline products have a higher E-modulus (modulus of elasticity) than amorphous mouldings. It was also established in further tests that amorphous poly(L-lactide) differs from crystalline poly(L-lactide) in its decomposition characteristics. Depending on the nature of the surgical implant which is to be produced it may therefore be necessary to produce either amorphous or crystalline products, as required, by injection moulding. The crystallinity can be influenced as described above by a suitable choice of injection conditions and/or in known manner by the addition of nucleating agents. Within the scope of this invention, for obvious reasons, only physiologically acceptable nucleating agents may be used such as salts of acceptable organic acids such as calcium citrate or high-melting polymers such as polyglycolic acid. The list is by way of example and is not restrictive. Crystalline products may also be obtained subsequently from amorphous mouldings by tempering. In the case of poly(L-lactide) simple warming for a long period (at least 30 minutes) to an elevated temperature (more than 70° C.) is sufficient to do this. The exact conditions of tempering may be optimally adjusted in accordance with the desired level of crystallisation.

Under certain conditions, orientation of the molecules will take place inside the moulding during the injection moulding process, with the effect of increasing the strength. In extreme cases, this will lead to an anisotropy of the mechanical properties, which is desirable for certain applications, i.e. the strength of an implant is greater in the longitudinal direction than in the transverse direction, for example. The strength in the longitudinal direction is higher than the strength in an otherwise identical isotropic moulding.

All the properties which have hitherto been mentioned for injection moulded articles also apply to articles produced by other processing steps used for thermoplastic polymers, such as extrusion, pressure melting, hot pressing and the like. The terms "injection moulding" and "injection moulded" are therefore by no means restrictive. The invention rather relates to implants which have been produced or modified in any way by thermoplastic deformation.

Polylactide according to this invention is poly(L-lactide) or poly(D-lactide), poly(L-lactide) being preferred. This invention also relates to copolymers of the two above-mentioned lactides with comonomers which lead to physiologically acceptable breakdown products. Such comonomers are D,L-lactide, meso-lactide, glycolide, dioxanone, trimethylene carbonate and other cyclic esters which are copolymerisable with lactide. Other suitable comonomers are α-, β- or γ-hydroxybutyric acid, α-, β- or γ-hydroxyvaleric acid and other hydroxy fatty acids ($C_{11}$ to $C_{25}$) such as stearic acid, palmitic acid, oleic acid, lauric acid and the like. However, D,L-lactide, meso-lactide, glycolide, β-hydroxybutyric acid and β-hydroxyvaleric acid are preferred, with D,L-lactide being particularly preferred. It has been found that the addition of comonomers causes a deterioration in the strength values. Thus, when choosing a copolymer which is suitable for each individual case, a compromise has to be reached between the reduced strength levels and improvements in other properties such as percentage elongation after fracture and breakdown characteristics. For the fields of application mentioned hereinbefore, the proportion of comonomer should be not more than 30%, preferably not more than 15%. Copolymers of L-lactide and D-lactide are suitable; polymers of L-lactide are preferred. Mouldings of poly(L-lactide-co-D,L-lactide) with inherent viscosities of between 1 and 3.5 dl/g are preferred, whilst inherent viscosities of between 1.4 and 2.5 dl/g are particularly preferred. The proportion of L-lactide in the copolymer is between 70 and 90%, preferably between 75 and 85%.

Example 3 describes the preparation of injection moulded test pieces consisting of poly(L-lactide-co-D,L-lactide) 90:10. Compared with Example 2 A, the product has an advantageously increased percentage elongation after fracture and also a higher tensile strength.

This invention relates in particular to mouldings (implants) with increased percentage elongation after fracture. It is known that the elongation after fracture of thermoplastics can be increased by the addition of low molecular liquids, low molecular solids or high molecular solids (=plasticiser effect). When liquid substances are added these are usually referred to plasticisers whilst if polymeric solids are added the term used is polymer blends. Normally (see H. G. Elias, Macromolecules; Hüthig & Wepf, Basel 1981, page 949) plasticisers increase the chain mobility. This does indeed lead to an increase in the percentage elongation after fracture but at the same time the glass transition temperature, modulus of elasticity, tear strength and hardness are reduced. Thus, in the present case, the addition of plasticisers could not be expected to have an advantageous effect on resorbable implants.

However, it was found, surprisingly, that the addition of certain liquids which are suitable as plasticisers results in a comparable strength with, at the same time, a significant increase in the percentage elongation after fracture. Other liquids which are also potentially suitable as plasticisers do not result in an increased elongation at break for a comparable strength (see Example 4). Suitable plasticisers are acetyltributyl-citrate and glycerol triacetate and mixtures of the two components.

The invention also relates to mouldings based on resorbable polymer mixtures, more particularly based on polylactide, containing as additive a high molecular solid (a polyester). The term polylactide according to this invention refers to poly(L-lactide), poly(D-lactide), poly(meso-lactide) and poly(D,L-lactide), mouldings based on poly(L-lactide) being preferred.

In further tests it was found, surprisingly, that the addition of certain high molecular solids (also known as additives according to the invention) to poly(L-lactide) not only results in an increase in the percentage elongation after fracture but will also significantly increase the tensile strength (Example 5). Whereas the increase in the elongation at break caused by the addition of a tougher component is to be expected, the simultaneous advantageous increase in tensile strength is a totally unexpected result. It is particularly advantageous that in a moulding (implant) made from poly(L-lactide) which contains the additive (solid) according to the invention, more than 75% of the tensile strength and significantly more than 3% elongation after fracture are maintained even after a period of 8 weeks under simulated physiological conditions (37° C., Ringer solution). In accordance with the aims of the invention the high molecular solids must be degradable into physiologically acceptable products. Solids according to the invention are resorbable polyesters such as poly(D,L-lactide), poly(D-lactide), poly(meso-lactide), poly(glycolide), poly(trimethylene carbonate), poly(dioxanone), poly(caprolactone) and those consisting of any desired combinations of L-lactide, D-lactide, meso-lactide, D,L-lactide, glycolide, trimethylene carbonate, dioxanone, caprolactone and other co- and terpolymers which can be prepared from polymerisable cyclic esters, all of which are well known to those skilled in the art. Preferred high molecular solids are poly(D,L-lactide), poly (meso-lactide), poly(dioxanone) and poly(caprolactone). Poly(D,L-lactide) and poly(meso-lactide) are particularly preferred. Suitable copolymers include, for example:

poly(L-lactide-co-D,L-lactide)
poly(L-lactide-co-meso-lactide)
poly(L-lactide-co-glycolide)

poly(L-lactide-co-trimethylene carbonate)
poly(L-lactide-co-ε-caprolactone)
poly(D,L-lactide-co-meso-lactide)
poly(D,L-lactide-co-glycolide)
poly(D,L-lactide-co-trimethylene carbonate)
poly(D,L-lactide-co-ε-caprolactone)
poly(meso-lactide-co-glycolide)
poly(meso-lactide-co-trimethylene carbonate)
poly(meso-lactide-co-ε-caprolactone)
poly(glycolide-co-trimethylene carbonate)
poly(glycolide-co-ε-caprolactone)

The amount of high molecular solid added may generally range from 1 to 50%, and up to 85% in special cases. However, added amounts of between 5 and 35%, particularly 5 to 25%, are preferred. When small amounts are added, the inherent viscosity of the high molecular solid added is not critical. Generally, the viscosity of the additive is in the range of viscosity of the basic polymer as defined hereinbefore. If amounts of 10% or more are added, however, the inherent viscosity should be more than 1 dl/g (25° C., chloroform). If copolymers are used, their sequence is not critical. Statistical copolymers and block copolymers are equally suitable.

The preferred copolymer is poly(L-lactide-co-D,L-lactide).

Copolymers which contain L-lactide as a component preferably contain at least 70% of the L-component, but preferably not more than 95%. A particularly preferred range is from 75 to 85% of the L-component in the copolymer.

If the proportion of poly-L-lactide in the polymer mixture is more than 85%, the proportion of L-lactide in the copolymer should be not more than 90%.

Other preferred mouldings are those obtained from a polymer mixture containing poly(L-lactide-co-D,L-lactide) with an amount of 70 to 95% of L-lactide in the copolymer and poly(D,L-lactide) containing an amount by weight of 1 to 85%, preferably 5 to 35, especially 15 to 35 poly(D,L-lactide) in the polymer mixture and mouldings consisting of poly(L-lactide) and poly(D,L-lactide) with an amount by weight of 5 to 85%, preferably 15 to 50%, especially 15 to 35% of poly(D,L-lactide) in the polymer mixture.

There are various ways of preparing the mixtures of poly(L-lactide) and the additives described above according to the invention. On the one hand, mixtures of the two components may be used directly in the injection moulding process, whilst on the other hand the mixture of the two components can be worked into granules which are then injection moulded.

The invention thus also relates to the production of mouldings by injection moulding, in which polylactide such as poly(L-lactide) or a copolymer of L-lactide and D,L-lactide containing up to 30%, preferably between 5 and 15%, of D,L-lactide with a polymeric additive or granules of a mixture of the two are used. Injection mouldings are produced which have both strength and toughness. It is particularly worth noting that the strength of the polymer mixtures according to the invention is significantly higher and remains at a high level over a period of 8 weeks, as required.

The Examples which follow are intended to illustrate the invention.

The injection moulding machine used is a fully hydraulic Anker Demag piston machine (piston diameter 21 mm, shutting force 150 KN). The conditions for injection moulding the various polymers and polymer mixtures are shown in Table 6. 40° C. was used as the temperature of the tool for all the types of plastic whilst the speed of injection used was the maximum possible. The strength tests were carried out using a universal testing machine of the type JJ Lloyds T 5002. The shape of the test pieces tested for tensile strength was similar to that of test piece no. 4 in DIN 53455, the test pieces being 3 mm thick.

EXAMPLES

Example 1

Preparation of Samples From Poly(L-lactide)

Poly(L-lactide) test rods (2×3×25 mm) were produced by injection moulding from granules having an inherent viscosity of 7.8 dl/g and by machining from block material (i.v. 7.9 dl/g). The bending strength of these test pieces was determined in the form as delivered and after sterilisation and as a function of the period of implantation in accordance with DIN 53452. Rats were used as the test animals. The results are shown in Table 1.

TABLE 1

Bending strength of test pieces of poly(L-lactide) after implanting in rats (N/mm²)

| Test series | Material | State of processing |
|---|---|---|
| No. 1 | poly(L-lactide) (i.v. 7.8 dl/g) | injection moulded, i.v. 3.08 dl/g sterilised, amorphous |
| No. 2 | poly(L-lactide) (i.v. 2.9 dl/g) | injection moulded, i.v. 1.65 dl/g sterilised, amorphous |
| No. 3 | poly(L-lactide) | block polymer, i.v. 7.9 dl/g, sterilised, crystalline |

| Test series | Period of implantation (weeks) | | | | |
|---|---|---|---|---|---|
| | 0 | 2 | 4 | 6 | 8 |
| No. 1 | 130.3 | 120.2 | 112.5 | 107.1 | 106.3 |
| No. 2 | 118.3 | 109.3 | 107.6 | 105.4 | 114.7 |
| No. 3 | 118.8 | 78.8 | 54.7 | 32.3 | 22.0 |

| Test series | 12 | 20 | 24 | 32 |
|---|---|---|---|---|
| No. 1 | 99.6 | 65.1 | 51.3 | 19.2 |
| No. 2 | 124.0 | 77.5 | 68.0 | 30.2 |
| No. 3 | 15.5 | 9.8 | 7.4 | 4.6 |

Example 2

Initial Strength of Injection Moulded Samples of Poly(L-lactide) With a Low Inherent Viscosity Test pieces for the tensile test according to DIN 53455 (testing speed 10 mm/min) were produced from poly(L-lactide) granules (i.v. 2.91 dl/g) in an injection moulding machine. The properties of these test pieces are shown in Table 2 A. The bending strength was determined as described in Example 1.

Table 2 B shows comparison results for test pieces obtained from polymer blocks.

TABLE 2 A

| Mechanical properties of injection moulded samples | |
|---|---|
| Inherent viscosity | 1.45 dl/g |
| Tensile strength | 46.4 N/mm² |
| Elongation after fracture | 0% |
| Bending strength | 118.3 N/mm² |

TABLE 2 B

| Mechanical properties of samples obtained from polymer blocks | | | |
|---|---|---|---|
| Inherent viscosity | 7.9 | 7.4* | 3.7* dl/g |
| Tensile strength |  | 58.2 | 28.8 N/mm² |
| Bending strength | 118.8 |  | N/mm² |

*from EP 0108635

Example 3

Mouldings Obtained From Poly(L-lactide-co-D,L-lactide)

Granules of poly(L-lactide-co-D,L-lactide) 90:10 (i.v. 7.0 dl/g) were used to produce injection moulded test pieces for the tensile test according to DIN 53455 (test speed: 10 mm/min). The properties of these test pieces are shown in Table 3.

TABLE 3

| Inherent viscosity | 2.10 dl/g |
|---|---|
| Tensile strength | 51.6 N/mm² |
| Elongation after fracture | 2.0% |

Example 4

Influence of Low Molecular Plasticisers on Poly(L-lactide)

8.6% acetyltributylcitrate were incorporated in poly(L-lactide). The inherent viscosity of the granules produced therefrom was 1.72 dl/g. Injection moulded test pieces were prepared from these granules for the tensile test according to DIN 53455 (test speed: 10 mm/min).

Table 4 summarises the properties:

TABLE 4

| Inherent viscosity | 1.40 dl/g |
|---|---|
| Tensile strength | 46.2 N/mm² |
| Elongation after fracture | 3.0% |

A poly(L-lactide) produced analogously and containing 10% butyl butyryl lactate was found to have a tensile strength of 46.2N/mm², but an unchanged elongation after fracture of 0%. The addition of 1.5% or 4.7% triethyl citrate resulted in lower tensile strengths of 14.2N/mm² and 9.7N/mm², respectively, compared with the pure poly(L-lactide). The elongation after fracture remained unchanged at 0%.

Example 5

Influence of High Molecular Solids on Poly(L-lactide)

In the tensile test according to DIN 53455, injection moulded test pieces of polymer mixtures consisting of poly(L-lactide) and poly(D,L-lactide) were tested at a test speed of 10 mm/min. The mechanical properties as a function of the mixing ratio were assembled in Table 5 A. Table 5 B shows the change in the mechanical properties after hydrolysis in Ringer solution at 37° C. Comparative values for hydrolysed tensile test pieces of injection moulded poly(L-lactide) are also given.

TABLE 5 A

Tensile test on injection moulded test pieces consisting of poly(L-lactide) and polymer mixtures of poly(L-lactide)/poly(D,L-lactide) (PLLA/PDLLA) (DIN 53455; average x; n = 5)

| Material | Tensile strength x [N/mm²] | Elongation η* after fracture x [%] | dl/g |
|---|---|---|---|
| PLLA | 46.4 | 0 | 1.45 |
| PLLA/PDLLA 90/10 | 63.3 | 3.8 | 1.75 |
| PLLA/PDLLA 80/20 | 64.5 | 3.6 | 1.82 |
| PLLA/PDLLA 70/30 | 59.7 | 5.2 | 1.54 |
| PLLA/PDLLA 50/50 | 55.3 | 2.4 | 1.47 |
| PLLA/PDLLA 30/70 | 55.0 | 6.0 | 1.65 |

PLLA = poly(L-lactide)
PDLLA = poly(D,L-lactide)
*inherent viscosity

TABLE 5 B

Tensile test on injection moulded test pieces obtained from polymer mixtures of poly(L-lactide) and poly(D,L-lactide) and poly(L-lactide) after hydrolysis in Ringer solution at 37° C. (DIN 53455; average x; n = 5)

| | | | Hydrolysis time in weeks | | | |
|---|---|---|---|---|---|---|
| Material | | | 0 | 4*⁾ | 8*⁾ | 12*⁾ |
| PLLA/PDLLA 90/90 | Tensile strength (N/mm²) | x | 63.3 | 56.3 | 53.6 | 52.8 |
| | Elongation after fracture (%) | x | 3.8 | 16.0 | 6.0 | 5.0 |
| PLLA/PDLLA 30/10 | Tensile strength (N/mm²) | x | 59.7 | 50.7 | 49.0 | 46.9 |
| | Elongation after fracture (%) | x | 5.2 | 9.3 | 9.0 | 6.5 |
| PLLA | Tensile strength (N/mm²) | x | 46.4 | 37.6 | 35.4 | 29.0 |
| | Elongation after fracture (%) | x | 0 | 0 | 0 | 0 |

*⁾samples were measured in water-saturated state.

TABLE 6

Injection moulding conditions for tensile test pieces various polymers and polymer mixtures

| Polymer | Cylinder Temp °C. | Injection Time (s) | Injection Pressure (bar) | Holding Pressure (bar) | Holding Pressure Time (s) | Cooling Time (s) |
|---|---|---|---|---|---|---|
| PLLA | 190° | 10 | 1120 | 600 | 1.5 | 15 |

TABLE 6-continued

Injection moulding conditions for tensile test pieces various polymers and polymer mixtures

| Polymer | Cylinder Temp °C. | Injection Time (s) | Injection Pressure (bar) | Holding Pressure (bar) | Holding Pressure Time (s) | Cooling Time (s) |
|---|---|---|---|---|---|---|
| Poly (L-lactide-co-D,L-lactide) 90/10 | 238° | 10 | 1110 | 600 | 1.5 | 15 |
| PLLA + 8.6% acetyltributyl-citrate | 185° | 10 | 1130 | 600 | 1.5 | 15 |
| PLLA + 10% butylbutyryl lactate | 185° | 10 | 1150 | 600 | 1.5 | 15 |
| PLLA + 1.5% triethylcitrate | 180° | 10 | 1130 | 600 | 1.5 | 15 |
| PLLA + 4.7 triethylcitrate | 180° | 10 | 1130 | 600 | 1.5 | 1.5 |
| PLLA/PDLLA 90/10 | 190° | 10 | 1150 | 600 | 1.5 | 15 |
| PLLA/PDLLA 80/20 | 183° | 10 | 1150 | 600 | 1.5 | 15 |
| PLLA/PDLLA 70/30 | 175° | 10 | 1120 | 600 | 1.5 | 15 |
| PLLA/PDLLA 50/50 | 180° | 10 | 1150 | 600 | 1.5 | 15 |
| PLLA/PDLLA 30/70 | 175° | 10 | 1150 | 600 | 1.5 | 15 |

PLLA = poly(L-lactide)
PDLLA = poly(D,L-lactide)

We claim:

1. A process for producing resorbable moldings which comprises feeding a polylactide to an injection molding means operating under pressure and at a cylinder temperature of at least 175° C. to produce a resorbable molding having an inherent viscosity between 0.8 and 4.5 dl/g., an initial tensile strength of at least 45N/mm$^2$, and an initial bending strength of at least 90N/mm$^2$.

2. A resorbable molding produced by the process of claim 1.

3. The process of claim 1 in which the polylactide comprises poly(L-lactide), poly(D-lactide) or copolymers derived therefrom with other comonomers in the form of copolymerizable cyclic esters, the proportion of comonomer being not more than 30% by weight.

4. A resorbable molding produced by the process of claim 3.

5. The process of claim 3 in which the comonomer is selected from the group consisting of D,L-lactide, meso-lactide, glycolide, dioxanone, trimethylene carbonate, and lactones of β-hydroxybutyric acid and β-hydroxyvaleric acid.

6. A resorbable molding produced by the process of claim 5.

7. A process for producing resorbable moldings which comprises feeding a mixture of a polylactide or copolymers derived therefrom and solid particles of a high molecular weight resorbable polyester additive to an injection molding means operating under pressure to produce a resorbable molding.

8. The process claim 7 wherein the high molecular weight resorbable polyester additive is present in an effective amount to increase the tensile strength and percentage elongation after fracture.

9. The process of claim 8 wherein the additive is present in an amount of from 1 to 30% by weight of additive.

10. The process of claim 8 wherein the additive is present in an amount of from 1 to 15% by weight of additive.

11. A resorbable molding produced by the process of claim 7.

12. The process of claim 7 wherein the high molecular weight additive is selected from the group consisting of poly(D,L-lactide), poly(D-lactide), poly(meso-lactide), polyglycolide, polytrimethylene carbonate, polydioxanone, poly-ε-caprolactone and mixtures thereof.

13. The process of claim 7 wherein the additive is a copolymer selected from the group consisting of poly(L-lactide-co-D,L-lactide), poly(L-lactide-co-meso-lactide), poly(L-lactide-co-glycolide), poly(L-lactide-co-trimethylene carbonate), poly(L-lactide-co-ε-caprolactone), poly(D,L-lactide-co-meso-lactide), poly(D,L-lactide-co-glycolide), poly(D,L-lactide-co-trimethylene carbonate), poly(D,L-lactide-co-ε-caprolactone), poly(meso-lactide-co-glycolide), poly(meso-lactide-co-trimethylene carbonate), poly(meso-lactide-co-ε-caprolactone), poly(glycolide-co-trimethylene carbonate), poly(glycolide-co-ε-caprolactone) and mixtures thereof.

14. A process for producing resorbable moldings which comprises feeding a mixture of a polylactide and acetyltributyl-citrate, glycerol triacetate or mixtures thereof to an injection molding means operating under pressure to produce a resorbable molding.

15. A resorbable molding produced by the process of claim 14.

16. A resorbable moulding based on poly(lactide), or copolymers derived thereof, characterised in that it contains a high molecular additive consisting of a resorbable polyester in an effective amount in order to increase the tensile strength and percentage elongation after fracture, whereas poly (p-dioxaonone) is disclaimed as additive and the content of glycolide of the total composition is less than 65% by weight.

17. A moulding according to claim 16, characterised in that it consists of poly(L-lactide, poly(D-lactide) or copolymers derived therefrom with other comonomers in the form of copolymerisable cyclic esters the proportion of comonomer being not more than 30% by weight.

18. A moulding according to claim 17, characterised in that the comonomer is D,L-lactide, meso-lactide, glycolide, dioxanone, trimethylenecarbonate or a lactone of β-hydroxybutyric acid and/or β-hydroxyvaleric acid.

19. A resorbable moulding according to claims 16, 17 or 18 characterised in that it contains poly(L-lactide) or poly (L-lactide-co-D,L-lactide).

20. A resorbable moulding according to claim 19, characterised in that the high molecular additive is poly(D,L-lactide), poly(D-lactide), poly(meso-lactide), polyglycolide, polytrimethylene carbonate, polycaprolactone or mixtures thereof.

21. A resorbable moulding according to claims 16, 17 or 18 characterised in that the additive is a copolymer selected from the group consisting of poly(L-lactide-co-D,L-lactide)

poly(L-lactide-co-meso-lactide)
poly(L-lactide-co-glycolide)
poly(L-lactide-c-trimethylene carbonate)
poly(L-lactide-co-ε,-caprolactone)
poly(D,L-lactide-co-meso-lactide)
poly(D,L-lactide-co-glycolide)
poly(D,L-lactide-co-trimethylene carbonate)
poly(D,L-lactide-co-ε-caprolactone)
poly(meso-lactide-co-glycolide
poly(meso-lactide-co-trimethylene carbonate)
poly(meso-lactide-co-ε-caprolactone).

22. A resorbable moulding according to claim 16, characterised in that it contains 1 to 85% by weight of the additive.

23. A moulding according to claim 16, characterised in that it has a elongation after fracture of at least 2% in the initial state and under physiological conditions for a period of 8 weeks.

24. The moulding according to claim 17, wherein the proportion of comonomer is not more than 15% by weight.

* * * * *